(12) United States Patent
Dansie (10) Patent No.: US 11,051,723 B1
(45) Date of Patent: Jul. 6, 2021

(54) SINGLE REMOTE CONTROLLED ENCRYPTED WIRELESS VISUAL REINFORCEMENT AUDIOMETRY (VRA) SYSTEM THAT CONNECTS AN AUDIOMETER TO MULTIPLE PHYSICAL (3D) AND VIDEO VRA UNITS AND PREVENTS FREQUENCY OVERLAP BETWEEN MULTIPLE ADJACENT AND NEARBY VRA SYSTEMS

(71) Applicant: Joseph Evans Dansie, Provo, UT (US)

(72) Inventor: Joseph Evans Dansie, Provo, UT (US)

( * ) Notice: Subject to any disclaimer, the term of this patent is extended or adjusted under 35 U.S.C. 154(b) by 0 days.

(21) Appl. No.: 17/169,190

(22) Filed: Feb. 5, 2021

(51) Int. Cl.
*H03G 5/00* (2006.01)
*A61B 5/12* (2006.01)
*A61B 5/00* (2006.01)
*H04R 3/04* (2006.01)

(52) U.S. Cl.
CPC ............ *A61B 5/123* (2013.01); *A61B 5/6896* (2013.01); *A61B 5/6898* (2013.01); *H04R 3/04* (2013.01)

(58) Field of Classification Search
CPC ..... A61B 5/123; A61B 5/6896; A61B 5/6898; H04R 3/04
See application file for complete search history.

(56) References Cited

U.S. PATENT DOCUMENTS

| 6,302,698 B1 * | 10/2001 | Ziv-El | G09B 7/02 434/322 |
| 8,241,224 B2 * | 8/2012 | Keefe | A61B 5/121 600/559 |
| 9,399,111 B1 * | 7/2016 | Hanina | A61M 21/02 |
| 2004/0209232 A1 * | 10/2004 | Neumann | G09B 7/00 434/236 |
| 2005/0003330 A1 * | 1/2005 | Asgarinejad | G09B 7/02 434/20 |

\* cited by examiner

*Primary Examiner* — Simon King
(74) *Attorney, Agent, or Firm* — Plager Schack LLP; Mark H. Plager; Stephen Hallberg (57) ABSTRACT

A single remote controlled encrypted wireless visual reinforcement audiometry (VRA) system for use in estimating audiometric thresholds in young children or patients with developmental delays is disclosed. The visual reinforcement audiometry system utilizes an encrypted wireless signal that does not allow for frequency overlap on adjacent VRA systems, it does not require direct line of site transmission or placement of sensors throughout the audiometric suite.

17 Claims, 8 Drawing Sheets

SINGLE REMOTE CONTROLLED ENCRYPTED WIRELESS VISUAL REINFORCEMENT AUDIOMETRY (VRA) SYSTEM THAT CONNECTS AN AUDIOMETER TO MULTIPLE PHYSICAL (3D) AND VIDEO VRA UNITS AND PREVENTS FREQUENCY OVERLAP BETWEEN MULTIPLE ADJACENT AND NEARBY VRA SYSTEMS

BACKGROUND

Embodiments of the invention described in this specification relate generally to visual reinforcement audiometry systems, and more particularly, to a single remote controlled encrypted wireless visual reinforcement audiometry (VRA) system that connects an audiometer to multiple adjacent physical (3D) and video VRA units and prevents frequency overlap between multiple adjacent and nearby VRA systems for use in estimating audiometric thresholds in young children or patients with developmental delays.

Conventional visual reinforcement audiometry (VRA) systems typically use either video-based VRA units or physical, three-dimensional (3D) VRA units, but not both at the same time or in the same set-up. Furthermore, the existing conventional VRA systems do not use both video VRA units and physical 3D VRA units from the same wireless remote, along with wireless control of the VRA system from an audiometer.

Also current VRA systems get frequency overlap on adjacent audiometric booths due to a lack of encrypted wireless signal or require placement of infrared sensors throughout the audiometric suite. Some of the other existing VRA systems utilize low frequency radio frequency (RF) that can be susceptible to interference and frequency overlap on VRA systems in adjacent areas. Still other systems that do not utilize RF instead utilize infrared (IR) and require placement of IR sensors throughout the audiometric suite or need direct, line of site transmission of the wireless signal. Other existing systems do not allow for control of more than three VRA reinforcement units with a single wireless remote control device, and therefore, either require two separate remotes or placement of two separate IR sensors in different locations to operate more than three VRA units.

Therefore, what is needed is a way to provide and use a single remote control in a visual reinforcement audiometry (VRA) system with more than three VRA units in an audiometric suite and to prevent wireless signal frequency overlap between adjacent and nearby VRA units that are wirelessly connected to an audiometer of the VRA system without requiring a direct line of sight for the wireless connections while also combining the use of both physical, three-dimensional (3D) VRA units and video VRA units to estimate audiometric thresholds in young children or patients with developmental delays.

BRIEF DESCRIPTION

Some embodiments of the invention include a novel single remote controlled encrypted wireless visual reinforcement audiometry (VRA) system that connects an audiometer to multiple adjacent physical (3D) and video VRA units and prevents frequency overlap between multiple adjacent and nearby VRA systems for use in estimating audiometric thresholds in young children or patients with developmental delays. In some embodiments, the single remote controlled encrypted wireless VRA system that connects an audiometer to multiple adjacent physical 3D and video VRA units and prevents frequency overlap between multiple adjacent and nearby VRA systems utilizes encrypted wireless signaling that does not allow for frequency overlap on adjacent VRA systems and does not require direct line of site transmission or placement of sensors throughout an audiometric suite in which the single remote controlled encrypted wireless VRA system is deployed for use in estimating audiometric thresholds in young children or patients with developmental delays.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments of the invention include a novel single remote controlled encrypted wireless visual reinforcement audiometry (VRA) system that prevents wireless signal frequency overlap between multiple adjacent physical (3D) and video VRA units deployed in an audiometric suite for use in estimating audiometric thresholds in young children or patients with developmental delays. In some embodiments, the single remote controlled encrypted wireless VRA system utilizes an encrypted wireless signal that does not allow for frequency overlap on adjacent VRA units and does not require direct line of site transmission or placement of sensors throughout the audiometric suite.

As stated above, conventional VRA systems typically use either video-based VRA units or physical, three-dimensional VRA units, but not both at the same time or in the same set-up. Furthermore, the existing conventional VRA systems do not use both video VRA units and physical 3D VRA units from the same wireless remote, along with wireless control of the VRA system from an audiometer. Also current VRA systems get frequency overlap on adjacent audiometric booths due to a lack of encrypted wireless signal or require placement of infrared sensors throughout the audiometric suite. Some of the other existing VRA systems utilize low frequency RF that can be susceptible to interference and frequency overlap on VRA systems in adjacent areas. Still other systems that do not utilize RF instead utilize IR and require placement of IR sensors throughout the audiometric suite or need direct, line of site transmission of the wireless signal. Other existing systems do not allow for control of more than three VRA reinforcement units with a single wireless remote control device, and therefore, either require two separate remotes or placement of two separate IR sensors in different locations to operate more than three VRA units. Embodiments of the single remote controlled encrypted wireless VRA system that prevents frequency overlap between multiple adjacent physical 3D and video VRA units described in this specification solve such problems by providing a way to control multiple VRA units, including simultaneously deployed combinations of both video VRA units and conventional physical 3D (or animated) VRA units, from a single wireless remote control device, as well as providing control of the VRA system directly through an audiometer, or any combination of those functions. The single remote controlled encrypted wireless VRA system that prevents frequency overlap between multiple adjacent physical 3D and video VRA units also utilizes wireless signals and data encryption to avoid frequency overlap on adjacent VRA units deployed in the VRA system without requiring any configuration or placement of infrared sensors.

Embodiments of the single remote controlled encrypted wireless VRA system that prevents frequency overlap between multiple adjacent physical 3D and video VRA units described in this specification differ from and improve upon currently existing VRA systems. In particular, some embodiments differ by providing support for a single remote control device in connection with multiple VRA units—which may include either or both of conventional physical 3D or animated VRA units and video-based VRA reinforcement units—with an audiometer available as well. By way of example, FIG. 1 conceptually illustrates an architecture of a single remote controlled encrypted wireless VRA system 100 that connects an audiometer to multiple adjacent physical 3D and video VRA units and prevents frequency overlap between multiple adjacent and nearby VRA systems for use in estimating audiometric thresholds in young children or patients with developmental delays. As shown in this figure, the single remote controlled encrypted wireless VRA system 100 includes a remote control device 110, an audiometer 120, a plurality of physical 3D VRA units 130, and a plurality of video VRA units 140. In some embodiments, the remote control device 110 is configured to send encrypted wireless signals to specific physical 3D VRA units 130 and specific video VRA units 140 according to unique addressing of the physical 3D VRA units 130 and the video VRA units 140 that correspond to buttons of the remote control device 110, which when depressed, specify options or commands to send to corresponding VRA units. In some embodiments, the remote control device 110 is configured for Bluetooth wireless communication. As such, the remote control device 110 is paired to the audiometer 120, which may be located nearby the remote control device 110 (as shown in this figure), or may be located in another room of an audiometric suite, such as is common in an audiometry facility. Also, each of the physical 3D VRA units 130 and the video VRA units 140 are configured to receive wireless Bluetooth signals from the remote control device 110 when paired with the remote control device 110. In this way, a specialist with the remote control device 110 can signal one of the physical 3D VRA units 130 or video VRA units 140 to provide a visual reward when a child or other subject provides a correct response to an audio stimulus. Further details of the remote control device 110 are described next.

Figure 2:
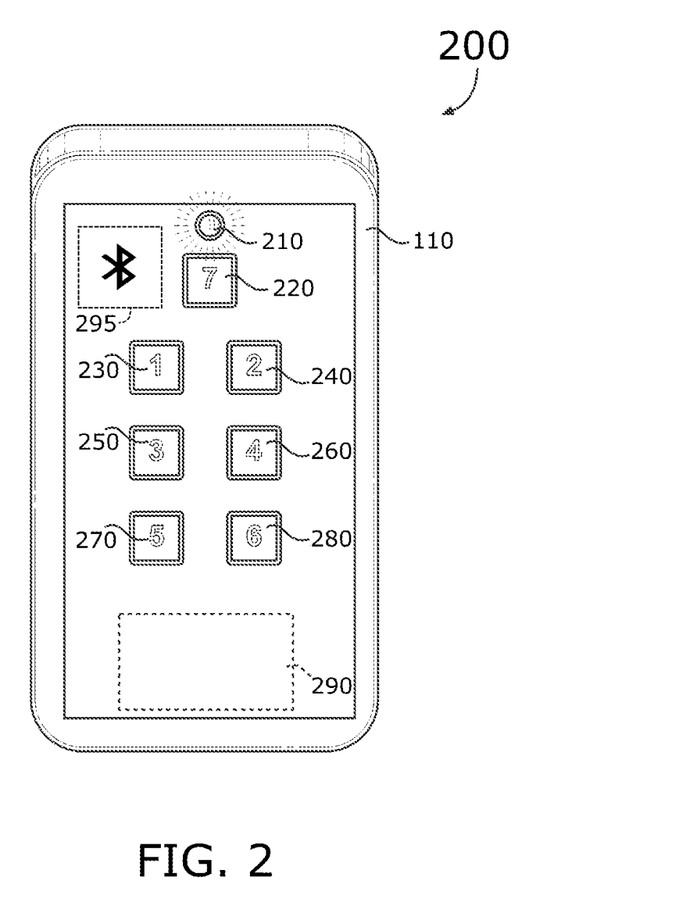
FIG. 2 conceptually illustrates a front view of a remote control device that is used in single remote controlled encrypted wireless VRA system that connects an audiometer to multiple adjacent physical 3D and video VRA units and prevents frequency overlap between multiple adjacent and nearby VRA systems in some embodiments.

By way of example, FIG. 2 conceptually illustrates a front view 200 of the remote control device 110 that is used in a single remote controlled encrypted wireless VRA system that connects an audiometer to multiple adjacent physical 3D and video VRA units and prevents frequency overlap between multiple adjacent and nearby VRA systems in some embodiments. As shown by the front view 200 in this figure, the remote control device 110 includes an LED light 210, a center button 220 (which is labeled "7" in this figure, but may have another label or no label at all, instead having a particular color of a particular significance or not), a top left button 230 (which is labeled "1" in this figure, but need not require any label, color, or anything particular), a top right button 240 (which is labeled "2" in this figure, but need not require any label, color, or anything particular), a middle left button 250 (which is labeled "3" in this figure, but need not require any label, color, or anything particular), a middle right button 260 (which is labeled "4" in this figure, but need not require any label, color, or anything particular), a bottom left button 270 (which is labeled "5" in this figure, but need not require any label, color, or anything particular), a bottom right button 280 (which is labeled "6" in this figure, but need not require any label, color, or anything particular), a battery compartment 290 (which is enclosed within an outer housing of the remote control device 110 and accessible from a back side of the remote control device 110), and a Bluetooth module and antenna 295 (which is also enclosed within the outer housing of the remote control device 110 and communicably and electronically connected to a printed circuit board embedded in the remote control device 110). The battery compartment 290 and the Bluetooth module and antenna 295 are not visible from the front view 200 of the remote control device 110 and, therefore, are shown in dashed outline. Although not shown in this figure, in some embodiments, the remote control device 110 includes an encryption-decryption module that encrypts and decodes wireless signals transmitted and/or received.

Also, it is possible for the data communication between the audiometer 120, the physical 3D VRA units 130, and the video VRA units 140 (and other devices, such as audio speakers) to be physically wired, or when used in connection with the remote control device 110, can be made partially or entirely wireless, such as by Bluetooth low energy (BLE) technology, with the wireless signals being encrypted (natively via Bluetooth and/or via the onboard encryption-decryption module of the remote control device's circuit board), so as to eliminate frequency overlap on adjacent VRA units and, especially, between different nearby single remote controlled encrypted wireless VRA systems. Furthermore, by interfacing with the audiometer 120, the single remote controlled encrypted wireless VRA system that prevents frequency overlap between multiple adjacent physical 3D and video VRA units provides another level of control from the audiometer 120 beyond the wireless remote control 110 itself, or, if preferred, by a combination of both the wireless remote control device 110 and the audiometer 120.

The use of Bluetooth wireless signaling is optimal for its ability to encrypt the signals being sent without resulting in frequency overlaps that would hinder signal reception/reading. This is an improvement over the currently existing VRA systems which typically rely on low frequency RF signaling. However, RF signaling does not work well because RF signals can cause interference and frequency overlap with other VRA systems in adjacent or neighboring rooms. Beyond RF, some conventional VRA systems utilize infrared (IR) signaling. Since IR signaling requires direct line of sight, these IR-based VRA systems are highly constrained in their set-up and configuration. This is not true of Bluetooth wireless technology. For example, utilizing IR in a conventional VRA system would not allow for wireless signaling to the audiometer in another room nearby the audiometric suite since the IR signaling requires a direct path (or "line of sight"). The work-around for IR-based systems is to include multiple IR sensors that are placed within the audiometric suite, with wiring placed from the IR sensors to the end device (VRA units or audiometer, for example). By contrast, the Bluetooth-enabled single remote controlled encrypted wireless VRA system that prevents frequency overlap between multiple adjacent physical 3D and video VRA units utilizes encrypted wireless signaling that does not allow for frequency overlap on adjacent VRA systems. Moreover, the Bluetooth wireless technology utilized by the single remote controlled encrypted wireless VRA system described in this specification does not require direct line of site transmission (like IR-based VRA systems) or placement of sensors throughout the audiometric suite.

Figure 3:
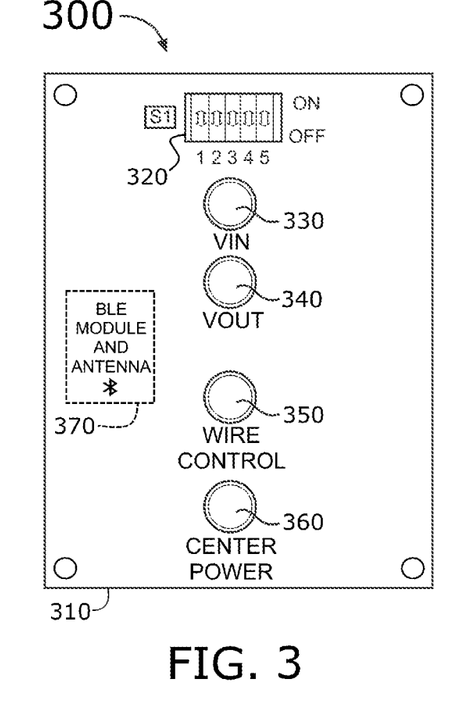
FIG. 3 conceptually illustrates a front view of a controller circuit board of a physical 3D VRA unit that interfaces with an audiometer in some embodiments.
Figure 4:
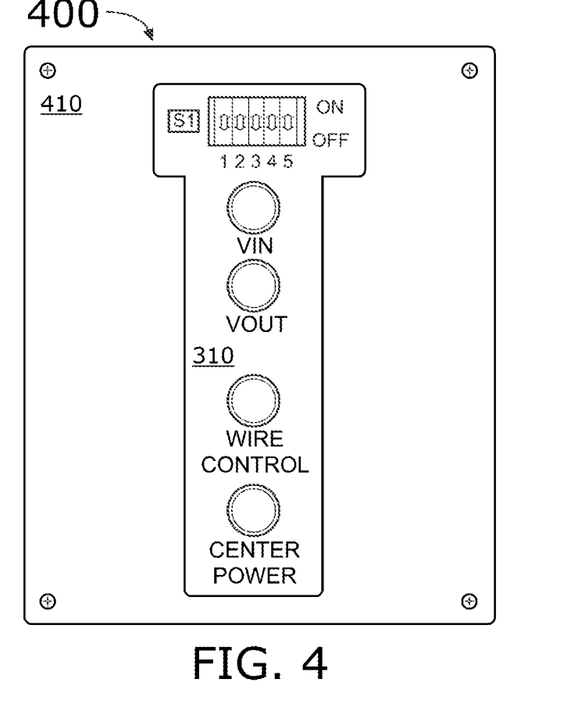
FIG. 4 conceptually illustrates a front view of a circuit board enclosure plate that covers the controller circuit board of the physical 3D VRA unit that interfaces with the audiometer in some embodiments.
Figure 5:
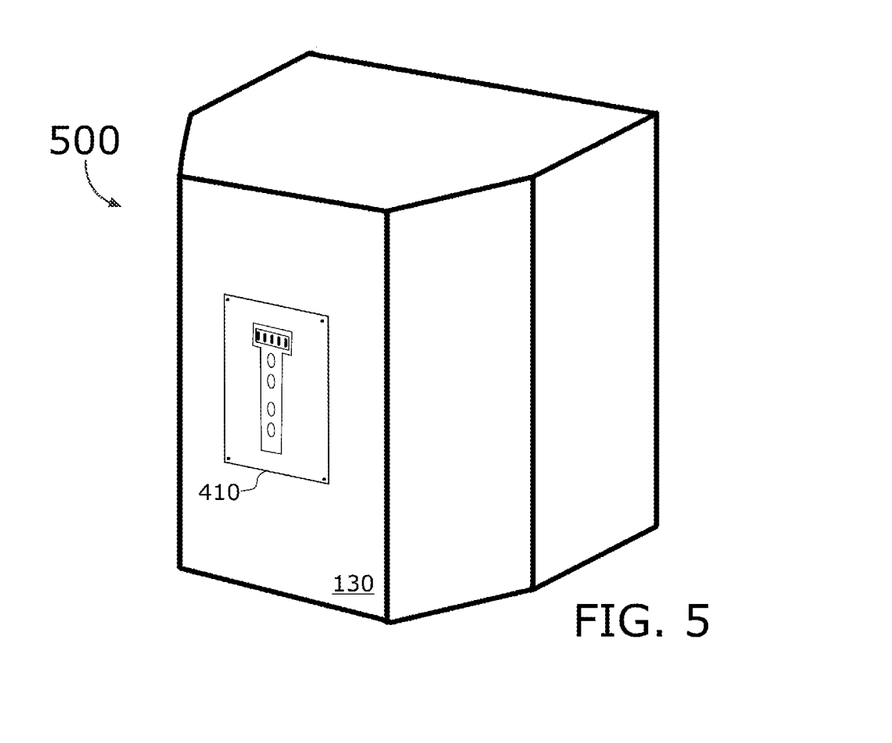
FIG. 5 conceptually illustrates a backside view of a physical 3D VRA unit in some embodiments showing the controller circuit board covered by the circuit board enclosure plate in some embodiments.

While many physical 3D VRA units are not equipped with wireless technology, the adaptation of such VRA units is next, by reference to FIGS. 3-5. First turning to FIG. 3, which conceptually illustrates a front view 300 of a controller circuit board 310 of a physical 3D VRA unit that interfaces with an audiometer in some embodiments. As shown by the front view 300 in this figure, the controller circuit board 310 of the physical 3D VRA unit includes a slide switch 320 for addressing and options of the physical 3D VRA unit, a power/voltage input connector 330, a power/voltage output connector 340, a wire control connector 350, a center power connector 360, and a Bluetooth module and antenna 370 (which is affixed to the opposing side of the front view 300 of the controller circuit board 310 and, therefore, is shown in dashed outline). In some embodiments, the controller circuit board 310 is attached to a back side of the physical 3D VRA unit. When the physical 3D VRA unit is a center VRA unit, it is may be hardwired to the audiometer 120 via the wire control connector 350. The physical 3D VRA unit can also be powered by a connection from the center power connector 360 to facility power. When powered, the controller circuit board 310 can output power/voltage to other VRA units, providing such power/voltage out of the power/voltage output connector 340 to the other VRA units in the single remote controlled encrypted wireless VRA system. The wire control connector 350 may not even be needed when, for example, the physical 3D VRA unit is entirely controlled by wireless Bluetooth signals, as supported by the Bluetooth module and antenna 370.

While not shown specifically in FIG. 3, in some embodiments, controller circuit board 310 further includes a decryption module to decode the encrypted wireless signals broadcast by the remote control device and determine whether the unique address of the physical 3D VRA unit is invoked in the encrypted signal. In some embodiments, the unique address of the particular physical 3D VRA unit is used, in part or whole, as a key (or part of a key) to decode the encrypted signal. Thus, when the encrypted signal can be successful decoded, the unique address of the particular physical 3D VRA unit would necessarily have been invoked and included in the encrypted wireless signal from the remote control device 110.

Also not shown in FIG. 3, yet relevant to the description above, in some embodiments, the controller circuit board 310 is included with the audiometer when the existing audiometer does not include wireless Bluetooth signaling and encryption modules/algorithms that would allow for encrypted communication between the remote control device, the audiometer, and the multiple VRA units.

In relation to the controller circuit board 310, and by way of example, FIG. 4 conceptually illustrates a front view 400 of a circuit board enclosure plate 410 that covers the controller circuit board 310 of the physical 3D VRA unit described above. In particular, the circuit board enclosure plate 410 covers the controller circuit board 310 when screwed through corner holes that attach both the controller circuit board 310 and the circuit board enclosure plate 410 to the back of the corresponding physical 3D VRA unit. This is demonstrated by reference to FIG. 5, which conceptually illustrates a backside view 500 of the physical 3D VRA unit showing the controller circuit board 310 affixed to the backside of the physical 3D VRA unit and covered by the circuit board enclosure plate 410.

Figure 1:
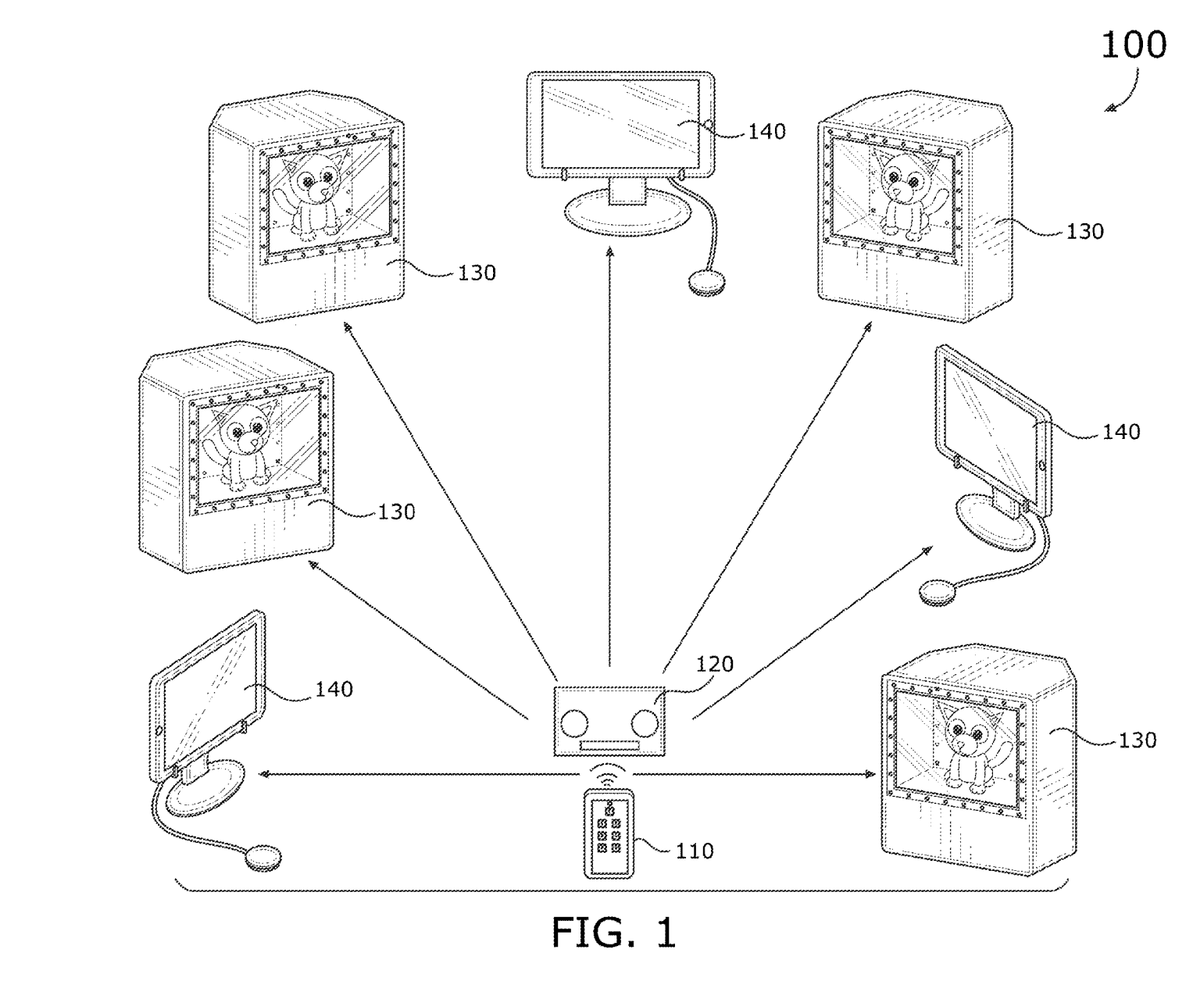
FIG. 1 conceptually illustrates an architecture of a single remote controlled encrypted wireless VRA system that connects an audiometer to multiple adjacent physical 3D and video VRA units in some embodiments and prevents frequency overlap between multiple adjacent and nearby VRA systems for use in estimating audiometric thresholds in young children or patients with developmental delays.

As demonstrated in the example shown in FIG. 1, the single remote controlled encrypted wireless VRA system 100 illustrated the deployment of seven total VRA units (both physical 3D units and video VRA units), an audiometer, and the remote control device. However, other configurations are possible for deployments of the single remote controlled encrypted wireless VRA system that prevents frequency overlap between multiple adjacent physical 3D and video VRA units of the present disclosure. For example, the following list of possible elements may be deployed in some embodiments of the single remote controlled encrypted wireless VRA system. This list of constituent elements is intended to be exemplary only and it is not intended that this list be used to limit the single remote controlled encrypted wireless VRA system that prevents frequency overlap between multiple adjacent physical 3D and video VRA units of the present application to just these elements. Persons having ordinary skill in the art relevant to the present disclosure may understand there to be equivalent elements that may be substituted within the present disclosure without changing the essential function or operation of the single remote controlled encrypted wireless VRA system that prevents frequency overlap between multiple adjacent physical 3D and video VRA units.

1. Wireless Remote
2. Right Primary Reinforcement Unit (video VRA unit, animated physical 3D unit, or non-animated physical 3D unit)
3. Left Primary Reinforcement Unit (video VRA unit, animated physical 3D unit, or non-animated physical 3D unit)
4. Right Secondary Reinforcement Unit (Optional) (video VRA unit, animated physical 3D unit, or non-animated physical 3D unit)
5. Left Secondary Reinforcement Unit (Optional) (video VRA unit, animated physical 3D unit, or non-animated physical 3D unit)
6. Centering Reinforcement unit, also referred to as a mid-line distractor unit (Optional) (typically a non-animated physical 3D unit, but may be a video VRA unit or an animated physical 3D unit)
7. Interface with audiometer (Optional)

Thus, the single remote controlled encrypted wireless VRA system that prevents frequency overlap between multiple adjacent physical 3D and video VRA units of the present disclosure generally works to control multiple VRA reinforcement units (e.g., 1-5 or more) and/or interface with an audiometer. The multiple VRA reinforcement units can include any combination of video VRA, conventional VRA, or animated VRA units. To make the single remote controlled encrypted wireless VRA system that prevents frequency overlap between multiple adjacent physical 3D and video VRA units of the present disclosure, one would add VRA reinforcement units to a wireless remote and/or audiometer. For instance, it would be possible to connect three units (primary Left, primary Right, and Center) to a remote control device (wireless or wired). In addition, other VRA units can be added, such as the secondary right and left VRA units. The VRA units may comprise any combination of 1-5 or more video VRA, conventional 3D or animated VRA units. These can be controlled by a single wireless remote control and/or through interface with an audiometer or any combination of those.

Whether the number of VRA units deployed in a single remote controlled encrypted wireless VRA system that prevents frequency overlap in wireless communication is seven VRA units, five VRA units, or less units, and whether the single remote controlled encrypted wireless VRA system that prevents frequency overlap between multiple adjacent physical 3D and video VRA units utilizes an audiometer and includes combinations of video VRA units with physical 3D VRA units (both/either animated/non-animated), the ability to use a single remote control to wirelessly control the system and all units makes for a unique ability not seen in conventional VRA systems. However, the VRA units that are deployed in a single remote controlled encrypted wireless VRA system need to be configured according to an addressing scheme that uniquely identifies each VRA unit (whether a physical 3D VRA unit or a video VRA unit). An example of such an addressing scheme is further described below, by reference to FIGS. 6-7.

Figure 6:
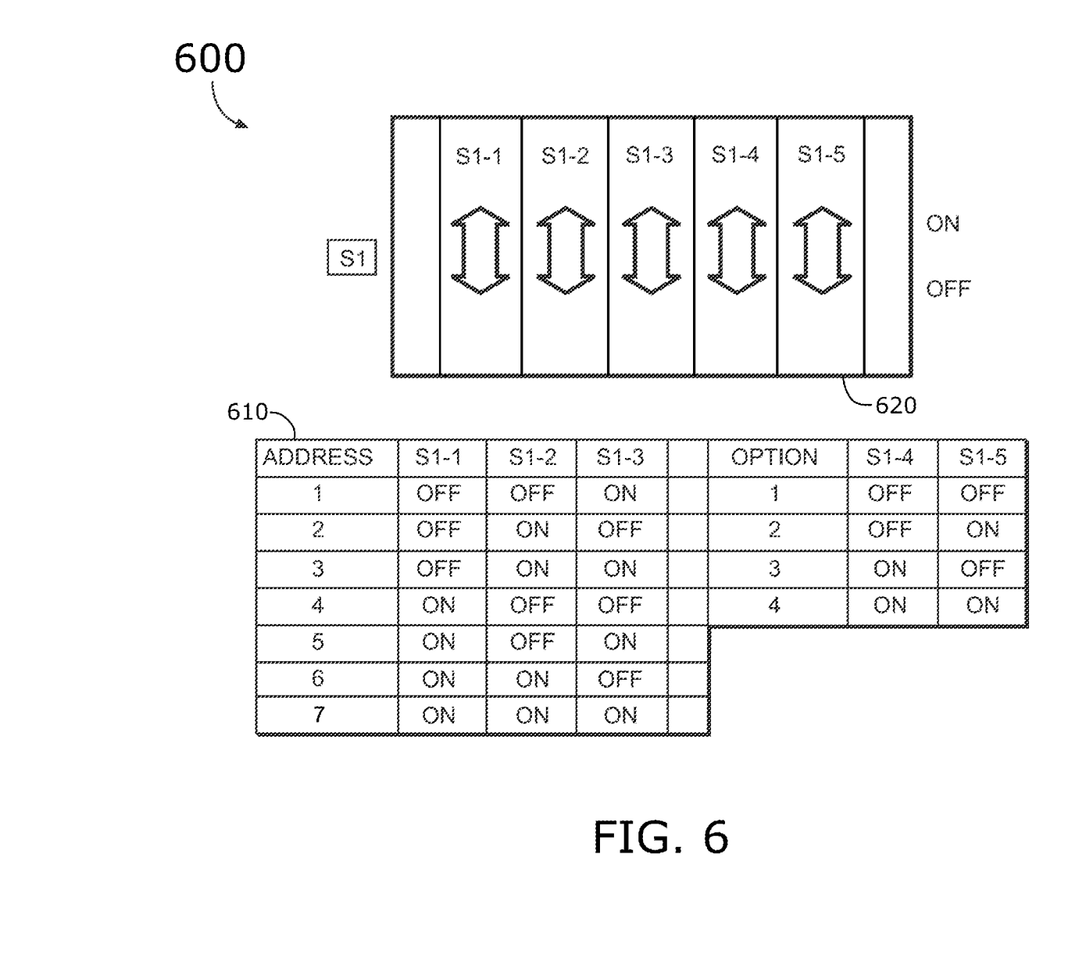
FIG. 6 conceptually illustrates a slide switch of a controller circuit board of a physical 3D VRA unit in some embodiments and a table of slide switch addressing and option configuration settings.

By way of example, FIG. 6 conceptually illustrates a slide switch of a controller circuit board of a physical 3D VRA unit in some embodiments and a table of slide switch addressing and option configuration settings 600. Specifically, as shown in this figure, a table of slide switch addressing and option configuration settings 610 relates to a slide switch S1 620 on which settings can be set to either "ON" or "OFF". For instance, when slide switch S1 620 is toggled to "OFF" for the first switch S1-1, "OFF" for the second switch S1-2, and "ON" for the third switch S1-3, then the corresponding VRA unit would be set to "ADDRESS 1" as shown in the table of slide switch addressing and option configuration settings 610. Similarly, when slide switch S1 620 is toggled to "OFF" for the first switch S1-1, "ON" for the second switch S1-2, and "OFF" for the third switch S1-3, then the corresponding VRA unit would be set to "ADDRESS 2" as shown in the table of slide switch addressing and option configuration settings 610. Yet another example is for a center VRA unit with "ADDRESS 7", specifically, when slide switch S1 620 is toggled to "ON" for the first switch S1-1, "ON" for the second switch S1-2, and "ON" for the third switch S1-3, as shown in the table of slide switch addressing and option configuration settings 610. While the labels shown on the buttons of the remote control device 110 described above by reference to FIG. 2 are merely conceptual in nature, and are not limiting in this disclosure, it may useful to think of the addressing in the table of slide switch addressing and option configuration settings 610 as being associated with the buttons of the remote control device 110 as labeled in FIG. 2.

In addition to the first, second, and third switches, S1-1, S1-2, and S1-3, respectively, the slide switch S1 620 shown in FIG. 6 also includes a fourth switch S1-4 and a fifth switch S1-5. In some embodiments, the fourth switch S1-4 and the fifth switch S1-5 are toggled in different ways to express one of four options for programs and settings that may be carried out by the VRA units to which they correspond. Specifically, the four options are shown in the table of slide switch addressing and option configuration settings 610 and include "OPTION 1" with the fourth switch S1-4 toggled "OFF" and the fifth switch S1-5 "OFF", "OPTION 2" with the fourth switch S1-4 toggled "OFF" and the fifth switch S1-5 "ON", "OPTION 3" with the fourth switch S1-4 toggled "ON" and the fifth switch S1-5 "OFF", and "OPTION 4" with the fourth switch S1-4 toggled "ON" and the fifth switch S1-5 "ON". Each of the four options may be configured to a specific program or option, such as continuous play of imagery/shuffling, video playback, LED light flashing, internal light display, animation of 3D object within housing of the corresponding physical 3D VRA unit or not, etc.

Figure 7:
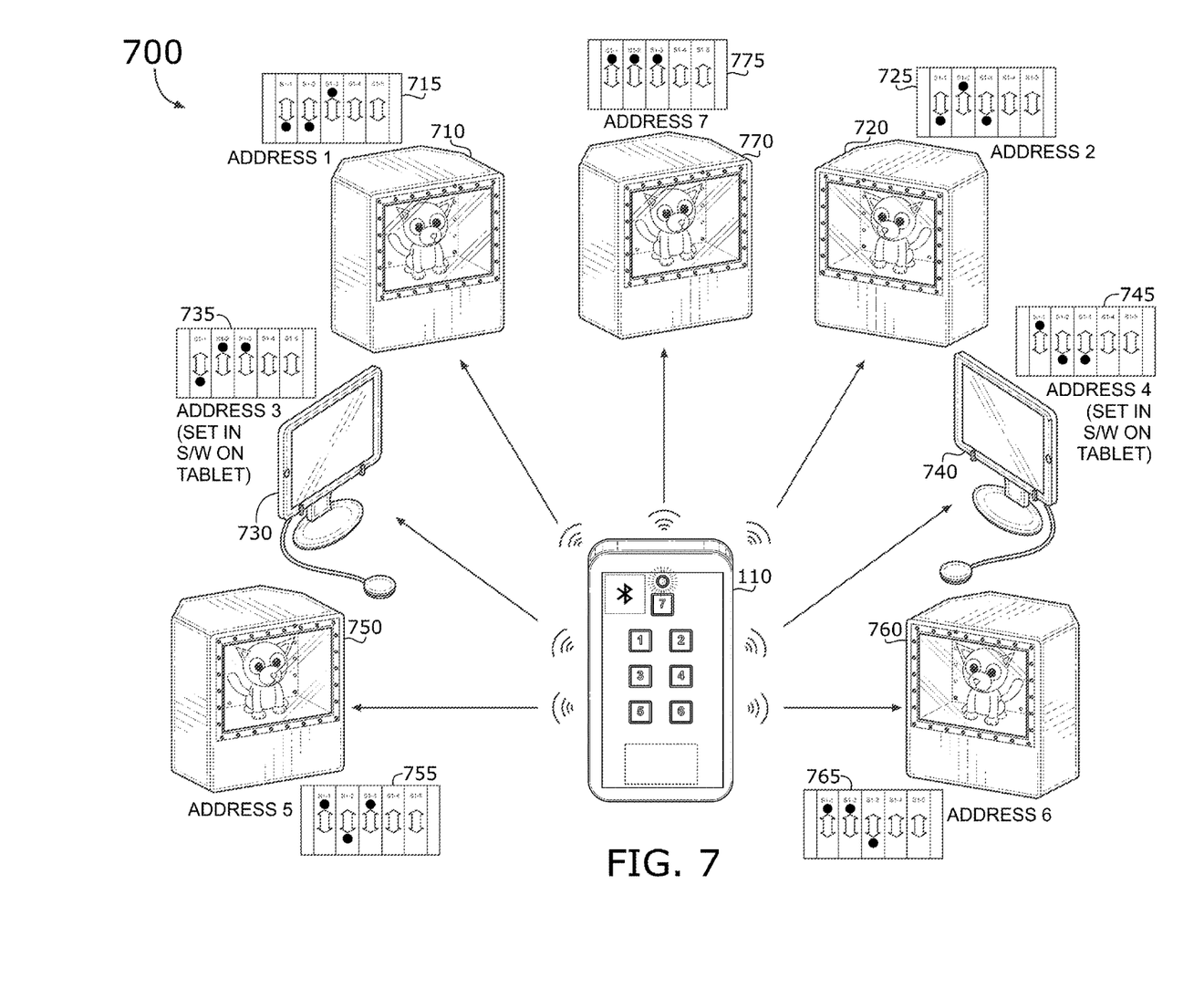
FIG. 7 conceptually illustrates slide switch addressing for several VRA units that are controlled by wireless encrypted signals from a remote control device used in a single remote controlled encrypted wireless VRA system in some embodiments.

Now turning to FIG. 7, slide switch addressing for several VRA units is shown in which the several VRA units include both video VRA units and physical 3D VRA units that are controlled by wireless encrypted signals from a single remote control device used in the single remote controlled encrypted wireless VRA system 700. While no audiometer is shown in this figure, a person of ordinary skill in the relevant art would appreciate that such an audiometer, if used, could be present in an adjacent room to the audiometric suite. As shown in this figure, the remote control device 110 is configured to wirelessly broadcast encrypted signals to each of seven VRA units according to the unique VRA unit address configured for each VRA unit. Specifically, the seven VRA units include (1) a first physical 3D VRA unit 710 that is set to "ADDRESS 1" by the toggle settings of the slide switch 715 of the controller circuit board affixed to the back of the first physical 3D VRA unit 710, (2) a second physical 3D VRA unit 720 that is set to "ADDRESS 2" by the toggle settings of the slide switch 725 of the controller circuit board affixed to the back of the second physical 3D VRA unit 720, (3) a third video VRA unit 730 that is a tablet computing device and is set to "ADDRESS 3" by user or system-saved settings of a user-configurable software slide switch 735 that is configured by way of a VRA software application that runs on the video VRA unit 730, (4) a fourth video VRA unit 740 that is a tablet computing device and is set to "ADDRESS 4" by user or system-saved settings of the user-configurable software slide 745 switch that is configured by way of the VRA software application that runs on the video VRA unit 740, (5) a fifth physical 3D VRA unit 750 that is set to "ADDRESS 5" by the toggle settings of the slide switch 755 of the controller circuit board affixed to the back of the fifth physical 3D VRA unit 750, (6) a sixth physical 3D VRA unit 760 that is set to "ADDRESS 6" by the toggle settings of the slide switch 765 of the controller circuit board affixed to the back of the sixth physical 3D VRA unit 760, and (7) a seventh physical 3D VRA unit 770 that is a center VRA unit and is set to "ADDRESS 7" by the toggle settings of the slide switch 775 of the controller circuit board affixed to the back of the seventh physical 3D VRA unit 770.

Thus, by using the single remote controlled encrypted wireless VRA system that prevents frequency overlap between multiple adjacent physical 3D and video VRA units of the present disclosure, it is possible to eliminate or decrease the likelihood of frequency overlap on adjacent VRA systems, eliminate the need of sensor placement and associated sensor wiring throughout the audiometric suite, instead providing a wireless mechanism that allows a person to control multiple VRA units (1-5 or more) from a single wireless remote and/or from an audiometer.

Although the physical 3D VRA units are adapted for encrypted wireless communication, as described above by reference to FIGS. 3-5, the video VRA units are often equipped with Bluetooth and other wireless technology. However, in order to ensure unique addressing for the broadcast Bluetooth signals, the video VRA units need to be configured according to the addressing scheme that uniquely identifies each VRA unit (and not to be configured in conflict with the physical 3D VRA units) deployed in a single remote controlled encrypted wireless VRA system. The example described above by reference to FIG. 7 makes mention of a VRA software application with a software slide switch that can be configured by a user or saved on the device for future use. This is further detailed below, by reference to FIGS. 8-9.

Figure 8:
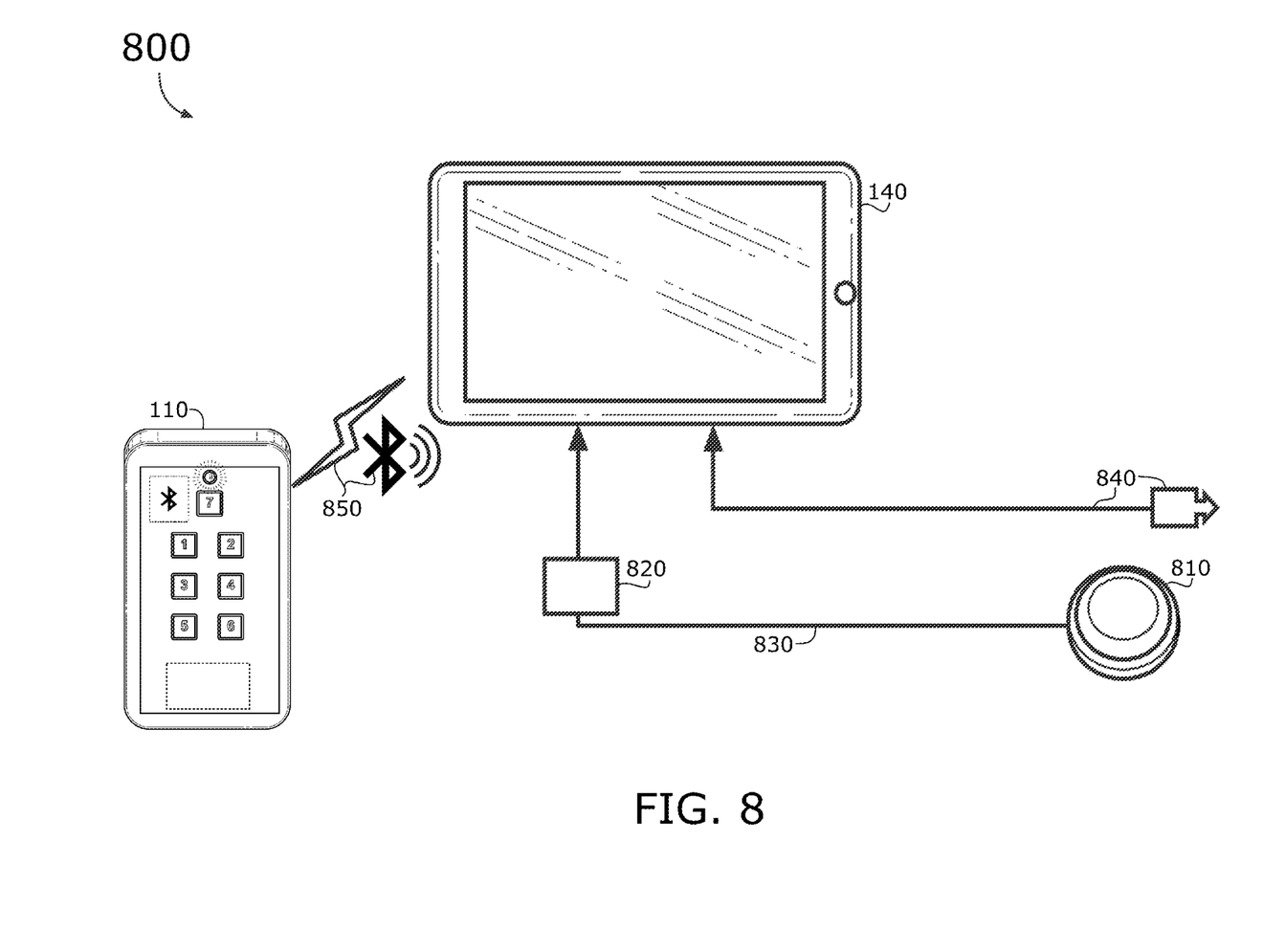
FIG. 8 conceptually illustrates a tablet computing device that is deployed as a video VRA unit in a single remote controlled encrypted wireless VRA system in some embodiments with a conditioned play audiometry (CPA) feedback button that allows a subject to respond to an audio stimulus and which is reinforced with rewarding visual imagery by wireless command from a remote control device.

By way of example, FIG. 8 conceptually illustrates a tablet computing device that is deployed as a video VRA unit in a single remote controlled encrypted wireless VRA system in some embodiments with a conditioned play audiometry (CPA) feedback button that allows a subject to respond to an audio stimulus and which is reinforced with rewarding visual imagery by wireless command from a remote control device 800. As shown in this figure, a tablet computing device is deployed as a video VRA unit 140 and is configured to receive encrypted Bluetooth wireless signals 850 from the remote control device 110. The tablet computing device as video VRA unit 140 is powered by facility power 840 (or charged battery from facility power 840). A human interface device is communicably hardwired to the tablet computing device. Specifically, the human interface device is a CPA feedback button 810 that is used by a subject, such as a child, during audiometric evaluation and testing. A CPA button interface 820 connects the CPA feedback button 810 to the tablet computing device for the video VRA unit 140 to receive the subject's responsive feedback 830 when he or she depresses the CPA feedback button 810 in response to an audio cue. While the CPA feedback button 810 is not required for using the single remote controlled encrypted wireless VRA system that prevents frequency overlap between multiple adjacent physical 3D and video VRA units of the present disclosure, the use by older children (e.g., ages 4-5 or so, at the discretion of the audiologist) can be beneficial. Therefore, while many of the example above demonstrate video VRA units having a connected CPA feedback button, it is understood that this is merely for conceptual illustration, and not intended to be absolute, required, or limiting of the single remote controlled encrypted wireless VRA system of the present disclosure.

Figure 9:
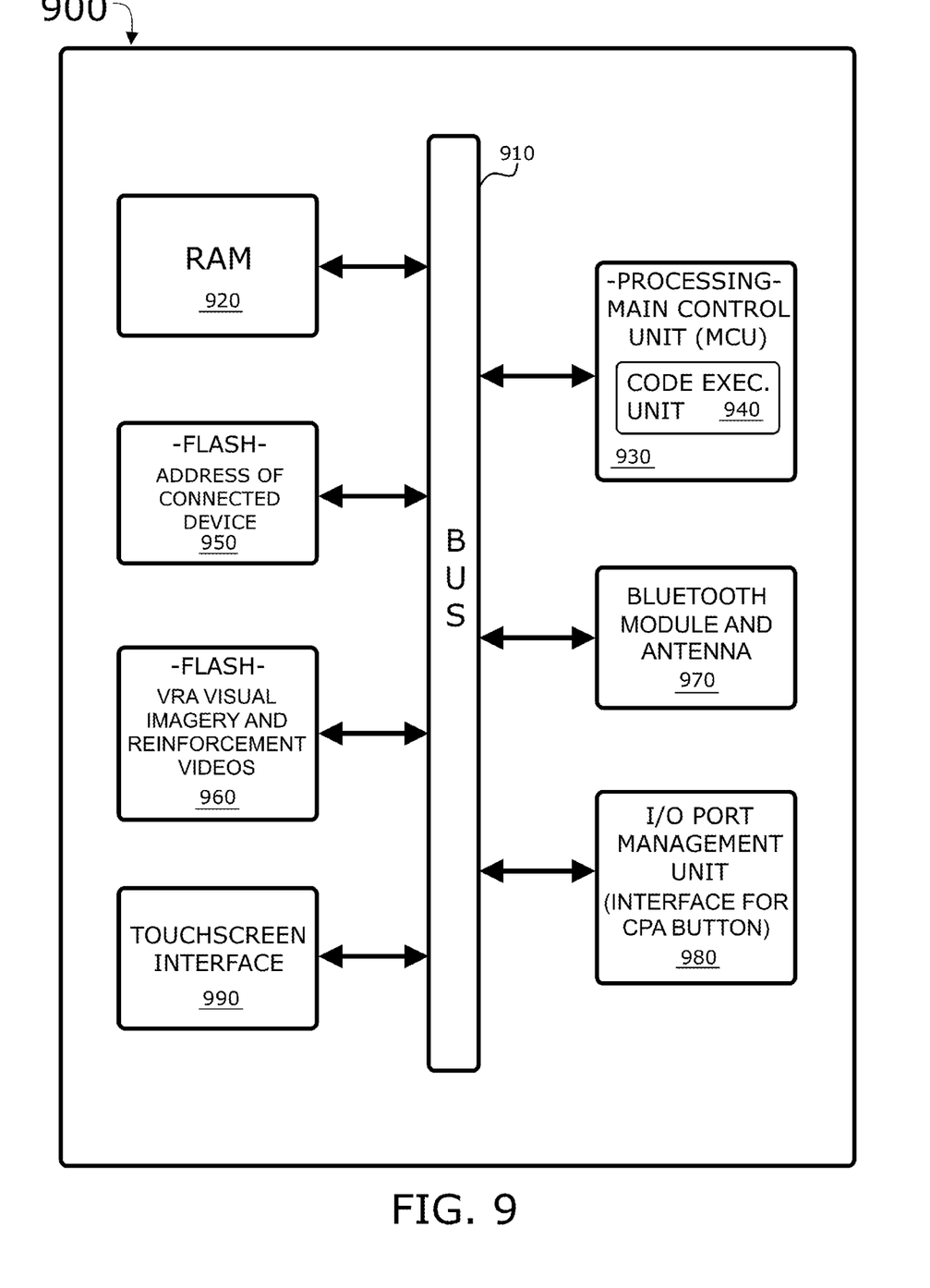
FIG. 9 conceptually illustrates a block diagram of a Bluetooth-enabled tablet computing device that is deployed as a video VRA unit in some embodiments of the single remote controlled encrypted wireless VRA system.

Now turning to another example, FIG. 9 conceptually illustrates a block diagram of a Bluetooth-enabled tablet computing device 900 that is deployed as a video VRA unit in some embodiments of a single remote controlled encrypted wireless VRA system. As shown in this figure, the Bluetooth-enabled tablet computing device 900 includes a bus 910, a random access memory (RAM) 920, a main control unit (MCU) 930 for runtime processing of the Bluetooth-enabled tablet computing device 900, a code execution unit 940 embedded within the MCU 930, a first persistent flash memory 950 that stores a unique video VRA unit address that uniquely identifies the Bluetooth-enabled tablet computing device 900 as a valid video VRA unit in the single remote controlled encrypted wireless VRA system, a second persistent flash memory 960 that stores software code for the VRA software application and corresponding VRA visual imagery and reinforcement videos, a Bluetooth module and antenna 970 that pairs with a remote control device (used in the single remote controlled encrypted wireless VRA system in which the tablet computing device is deployed) and receives encrypted wireless Bluetooth signals that correspond to the unique video VRA unit address of the Bluetooth-enabled tablet computing device 900 stored in the first persistent flash memory 950 when the remote control device broadcasts the encrypted wireless Bluetooth signals with the unique video VRA unit address, an input/output (I/O) port management unit 980 that provides an interface for a human interactive CPA button used for response feedback from a subject being evaluated in connection with the single remote controlled encrypted wireless VRA system, and a touchscreen interface 990 to visually output the VRA visual imagery and reinforcement videos corresponding to the VRA software application and to display interactive graphical elements and configuration setting tools of the VRA software application including a user-configurable software slide switch that sets the unique address of the video VRA unit when the tablet computing device is deployed in the single remote controlled encrypted wireless VRA system.

In some embodiments, the software code for the VRA software application is executed at runtime by the code execution unit 940 of the MCU 930, which processes the software code to identify one or more images or videos among the corresponding VRA visual imagery and reinforcement videos to visually output onto the touchscreen interface 990 of the Bluetooth-enabled tablet computing device 900 in connection with accurate responses to conditioned play audiometry audio signals and sounds.

In some embodiments, the unique video VRA unit address stored in the first persistent flash memory 950 is configured and set by toggling virtual switch settings of the user-configurable software slide switch when that Bluetooth-enabled tablet computing device 900 is running the VRA software application with access to the configuration setting tools.

In some embodiments, the VRA software application includes encryption/decryption software code that decodes the encrypted wireless signal received from the remote control device. In some embodiments, the encryption/decryption software code of the VRA software application uses a decryption key that comprises the unique video VRA unit address and a unique remote control identifier that identifies the remote control device used in the single remote controlled encrypted wireless VRA system. In this way, a first Bluetooth-enabled tablet computing device and a second Bluetooth-enabled tablet computing device used in a first single remote controlled encrypted wireless VRA system (with a first remote control device) have unique decryption keys from each other, which are also different from decryption keys of another first Bluetooth-enabled tablet computing device (which may be configured with the same local address) and another second Bluetooth-enabled tablet computing device deployed in a second single remote controlled encrypted wireless VRA system (with a second, different remote control device). In other words, since the unique remote control identifier of the first remote control device used in the first single remote controlled encrypted wireless VRA system is different from the unique remote control identifier of the second, different remote control device used in the second single remote controlled encrypted wireless VRA system, there can be no frequency overlap of wireless signals or interference in decoding signals, even when the first Bluetooth-enabled tablet computing device in the first single remote controlled encrypted wireless VRA system is configured with the same unique video VRA unit address as the other first Bluetooth-enabled tablet computing device in the second, different single remote controlled encrypted wireless VRA system (and likewise for the second Bluetooth-enabled tablet computing device in each of the first and second single remote controlled encrypted wireless VRA systems).

As noted above, the unique video VRA unit address is part of the unique decryption key for decoding the encrypted wireless signal broadcast by the remote control device. However, when the remote control device broadcasts an encrypted signal with the unique video VRA unit address by which the Bluetooth-enabled tablet computing device 900 is configured for identification in the single remote controlled encrypted wireless VRA system, the unique video VRA unit address ensures that only the intended video VRA unit in the "local" single remote controlled encrypted wireless VRA system is able to decode the signal. Accordingly, when multiple single remote controlled encrypted wireless VRA systems are deployed in proximity of each other (such as in an office or audiometry facility), another unique identifier is used in combination with the unique video VRA unit addresses of each local single remote controlled encrypted wireless VRA system. Therefore, other encrypted wireless signals from other remote control devices used in other nearby, adjacent single remote controlled encrypted wireless VRA systems are not able to be decoded by units in the local system, and therefore, no interference of signals is experienced with multiple nearby/adjacent single remote controlled encrypted wireless VRA systems that may be deployed and used in an office or audiometry facility.

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the terms "software", "application", "VRA software application", "app", "tablet application", and "mobile app" (referred to below as "software") are meant to include firmware residing in read-only memory or applications stored in magnetic storage, which can be read into memory for processing by a processor, such as the processor of a mobile computing device or a mobile communication device, such as a smartphone, a hand-held computing device, or a tablet computing device (which may also be referred to simply as a "mobile device"), or the processor of a traditional computing device, such as a server computer, a desktop computer, or a laptop computer (referred to simply as a "computer"). Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 10:
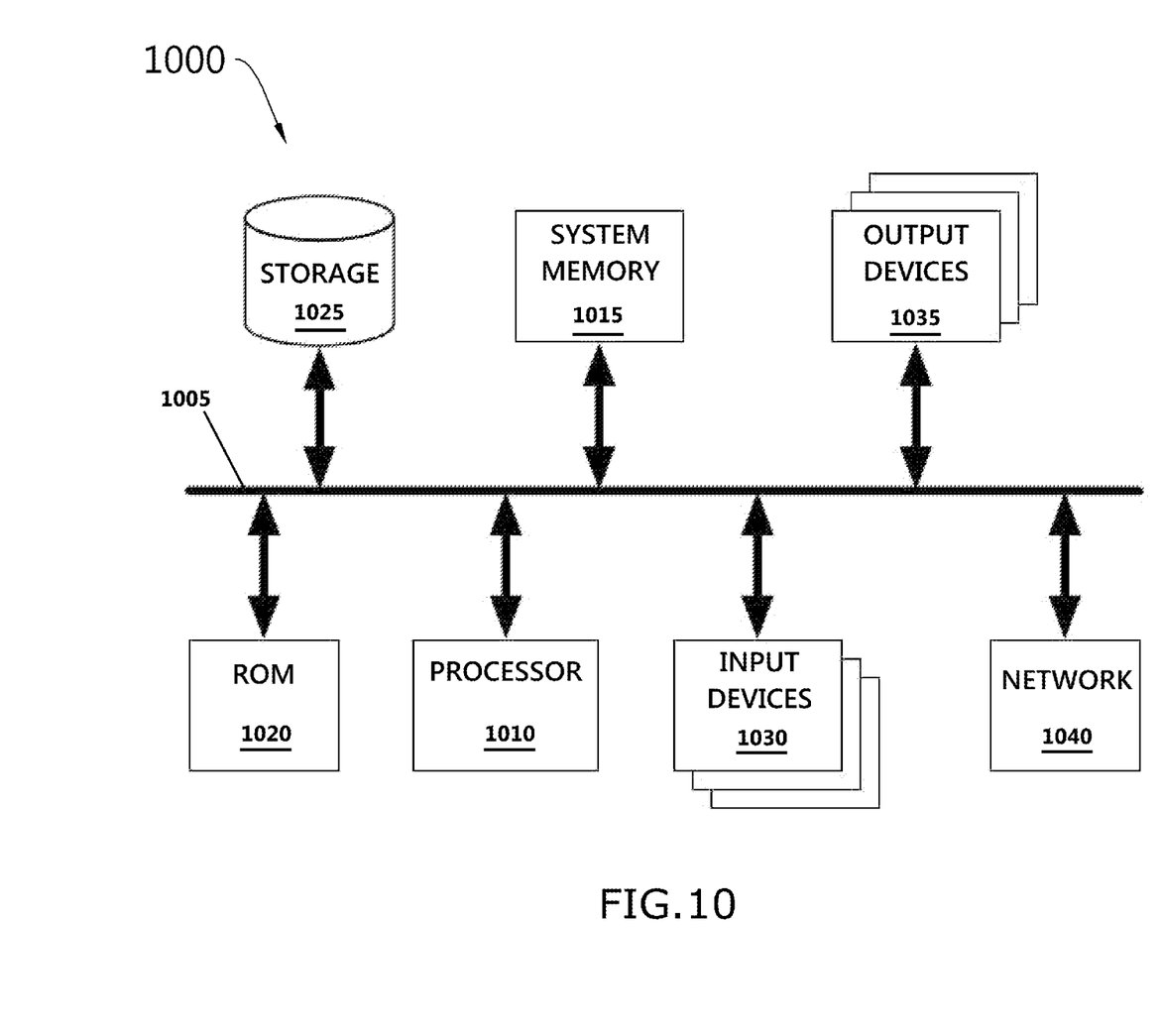
FIG. 10 conceptually illustrates an electronic system with which some embodiments of the invention are implemented.

FIG. 10 conceptually illustrates an electronic system 1000 with which some embodiments of the invention are implemented. The electronic system 1000 may be a computer, a circuit board, an audiometer, a remote control device, a custom printed circuit board (PCB), a mobile device, a tablet computing device, a smartphone, a personal digital assistance device (PDA), or any other sort of electronic device. Such an electronic system includes various types of computer readable media and interfaces for various other types of computer readable media. Electronic system 1000 includes a bus 1005, processing unit(s) 1010, a system memory 1015, a read-only memory 1020, a permanent storage device 1025, input devices 1030, output devices 1035, and a network 1040.

The bus 1005 collectively represents all system, peripheral, and chipset buses that communicatively connect the numerous internal devices of the electronic system 1000. For instance, the bus 1005 communicatively connects the processing unit(s) 1010 with the read-only memory 1020, the system memory 1015, and the permanent storage device 1025.

From these various memory units, the processing unit(s) 1010 retrieves instructions to execute and data to process in order to execute the processes of the invention. The processing unit(s) may be a single processor or a multi-core processor in different embodiments.

The read-only-memory (ROM) 1020 stores static data and instructions that are needed by the processing unit(s) 1010 and other modules of the electronic system. The permanent storage device 1025, on the other hand, is a read-and-write memory device. This device is a non-volatile memory unit that stores instructions and data even when the electronic system 1000 is off. Some embodiments of the invention use a mass-storage device (such as a magnetic or optical disk and its corresponding disk drive) as the permanent storage device 1025.

Other embodiments use a removable storage device (such as a floppy disk or a flash drive) as the permanent storage device 1025. Like the permanent storage device 1025, the system memory 1015 is a read-and-write memory device. However, unlike storage device 1025, the system memory 1015 is a volatile read-and-write memory, such as a random access memory. The system memory 1015 stores some of the instructions and data that the processor needs at runtime. In some embodiments, the invention's processes are stored in the system memory 1015, the permanent storage device 1025, and/or the read-only memory 1020. For example, the various memory units include instructions for processing appearance alterations of displayable characters in accordance with some embodiments. From these various memory units, the processing unit(s) 1010 retrieves instructions to execute and data to process in order to execute the processes of some embodiments.

The bus 1005 also connects to the input and output devices 1030 and 1035. The input devices enable the user to communicate information and select commands to the electronic system. The input devices 1030 include alphanumeric keyboards and pointing devices (also called "cursor control devices"). The output devices 1035 display images generated by the electronic system 1000. The output devices 1035 include printers and display devices, such as cathode ray tubes (CRT) or liquid crystal displays (LCD). Some embodiments include devices such as a touchscreen that functions as both input and output devices.

Finally, as shown in FIG. 10, bus 1005 also couples electronic system 1000 to a network 1040 through a network adapter (not shown). In this manner, the computer can be a part of a network of computers (such as a local area network ("LAN"), a wide area network ("WAN"), or an intranet), or a network of networks (such as the Internet). Any or all components of electronic system 1000 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

The above-described embodiments of the invention are presented for purposes of illustration and not of limitation. While the invention has been described with reference to numerous specific details, one of ordinary skill in the art will recognize that the invention can be embodied in other specific forms without departing from the spirit of the invention. For instance, many of the drawings conceptually illustrate devices, circuit boards, computing devices, or other electronic devices that perform runtime processes or methods, each with multiple steps. In each case, the specific operations of a process may not be performed in any particular order noted in the examples or descriptions. Specific operations may not be performed in one continuous series of operations, and different specific operations may be performed in different embodiments. Furthermore, each such process could configured via different options or specifications and may be implemented using several sub-processes, or as part of a larger macro process. Thus, one of ordinary skill in the art would understand that the invention is not to be limited by the foregoing illustrative details, but rather is to be defined by the appended claims.

I claim:

1. A single remote controlled encrypted wireless visual reinforcement audiometry (VRA) system that connects an audiometer to multiple adjacent physical 3D and video VRA units for use in estimating audiometric thresholds in young children or patients with developmental delays and prevents frequency overlap between multiple adjacent and nearby VRA systems, said single remote controlled encrypted wireless VRA system comprising:
 a remote control device that is configured to encrypt and transmit encrypted wireless signals to a plurality of address-based receiver units;
 a plurality of VRA units that are uniquely addressed as the plurality of address-based receiver units and configured to receive encrypted wireless communication from the remote control device; and
 an audiometer that is connected to the plurality of VRA units and configured to test audiometric thresholds of a subject by way of feedback and reinforcement through the plurality of VRA units.

2. The single remote controlled encrypted wireless VRA system of claim 1, wherein the plurality of VRA units comprise a physical 3D VRA unit and a video VRA unit.

3. The single remote controlled encrypted wireless VRA system of claim 2 further comprising a controller circuit board that includes a Bluetooth wireless module and antenna, wherein the controller circuit board is affixed to a back side of the physical 3D VRA unit.

4. The single remote controlled encrypted wireless VRA system of claim 3, wherein the controller circuit board further includes a slide switch to configure a unique address of the physical 3D VRA unit that is different from the address of each other VRA unit in the plurality of VRA units.

5. The single remote controlled encrypted wireless VRA system of claim 4, wherein the remote control device comprises a circuit board includes a Bluetooth wireless module and antenna and an encryption-decryption module to encrypt and decode wireless signals transmitted between the remote control device, the audiometer, and the plurality of VRA units.

6. The single remote controlled encrypted wireless VRA system of claim 5, wherein the encryption-decryption module encrypts a wireless signal broadcast with the unique address of the physical 3D VRA unit.

7. The single remote controlled encrypted wireless VRA system of claim 6, wherein controller circuit board further includes a decryption module to decode the encrypted wireless signal broadcast by the remote control device with the unique address of the physical 3D VRA unit.

8. The single remote controlled encrypted wireless VRA system of claim 2 further comprising a plurality of controller circuit boards, wherein a first controller circuit board includes a first Bluetooth wireless module and antenna and is affixed to a back side of the physical 3D VRA unit, wherein a second controller circuit board includes a second Bluetooth wireless module and antenna and is affixed to the audiometer.

9. The single remote controlled encrypted wireless VRA system of claim 2, wherein the plurality of VRA units comprise a first physical animated 3D VRA unit that includes an enclosed animation figure and a second physical non-animated 3D VRA unit that includes a stationary figure.

10. The single remote controlled encrypted wireless VRA system of claim 2, wherein a plurality of LED lights surround a front face of the physical 3D VRA unit.

11. The single remote controlled encrypted wireless VRA system of claim 2, wherein the video VRA unit comprises a tablet computing device that includes a VRA software application.

12. The single remote controlled encrypted wireless VRA system of claim 11, wherein the VRA software application includes a user-configurable software slide switch to uniquely address the video VRA unit distinctly from the addresses of other VRA units in the plurality of VRA units.

13. The single remote controlled encrypted wireless VRA system of claim 12, wherein the user-configurable software slide switch comprises a plurality of interactive virtual switch settings, wherein a combination of toggled virtual switch settings for a first virtual switch, a second virtual switch, and a third virtual switch in the plurality of interactive virtual switch settings defines a unique video VRA address that corresponds to the video VRA unit.

14. The single remote controlled encrypted wireless VRA system of claim 13, wherein the VRA software application includes software code which, when the VRA software application is executing on a main control processing unit of the tablet computing device, performs decryption of encrypted wireless Bluetooth signals broadcast by the remote control device.

15. The single remote controlled encrypted wireless VRA system of claim 14, wherein a non-conflicting encrypted wireless Bluetooth signal broadcast by the remote control device is based on at least the unique video VRA address corresponding to the video VRA unit and a unique remote control identifier associated with the remote control device.

16. The single remote controlled encrypted wireless VRA system of claim 15, wherein the non-conflicting encrypted wireless Bluetooth signal broadcast by the remote control device is different from a second system encrypted wireless Bluetooth signal broadcast by a second, different remote control device used in a second, adjacent remote controlled encrypted wireless VRA system, wherein the second system encrypted wireless Bluetooth signal is based on at least a target unique address of a target VRA unit in the second, adjacent remote controlled encrypted wireless VRA system and a second, different unique remote control identifier associated with the second, different unique remote control device used in the second, adjacent remote controlled encrypted wireless VRA system.

17. The single remote controlled encrypted wireless VRA system of claim 11, wherein the video VRA unit comprises a conditioned play audiometry (CPA) button that is connected to the tablet computing device by way of a CPA button interface, wherein the CPA button allows a subject to interactively provide responsive feedback by pressing the CPA feedback button in response to an audio cue.

\* \* \* \* \*